(12) United States Patent
Krahn

(10) Patent No.: US 6,323,659 B1
(45) Date of Patent: *Nov. 27, 2001

(54) MATERIAL FOR IMPROVED SENSITIVITY OF STRAY FIELD ELECTRODES

(75) Inventor: John Raymond Krahn, Niskayuna, NY (US)

(73) Assignee: General Electric Company, Schenectady, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/407,312

(22) Filed: Sep. 28, 1999

Related U.S. Application Data (63) Continuation-in-part of application No. 09/069,448, filed on Apr. 29, 1998, now Pat. No. 6,114,863.

(51) Int. Cl.[7] .......................... H01H 31/12; G01R 27/26
(52) U.S. Cl. .......................... 324/554; 324/664; 324/674
(58) Field of Search .................. 324/554, 658, 324/663, 664, 667, 683, 689, 724, 674; 361/286

(56) References Cited

U.S. PATENT DOCUMENTS

| | | |
|---|---|---|
| 3,870,951 | 3/1975 | Brown et al. .................. 324/61 P |
| 3,940,754 | 2/1976 | Weber . |
| 3,966,973 | 6/1976 | Henry et al. . |
| 4,228,393 | 10/1980 | Pile . |
| 4,352,059 | 9/1982 | Suh et al. .................. 324/61 R |

(List continued on next page.)

FOREIGN PATENT DOCUMENTS

| | | |
|---|---|---|
| 1465417 | 2/1977 | (DE) . |
| 0 753 438 | 1/1997 | (EP) . |
| 0 953 839 | 11/1999 | (EP) . |
| 0421881 | 10/1990 | (FR) . |
| 2217461 | 10/1989 | (GB) . |
| 2298923 | 9/1996 | (GB) . |
| 9628741 | 9/1996 | (WO) . |

OTHER PUBLICATIONS

AF Friedeck, "Detecting and Locating Stator Cooling–Water Leaks", Rotating Machinery, Doble Engineering Company, 60AIC93, 1993, pp. 7–9.113 7–9.10. Missing Month.
Viktor Kogan et al., "On Line Water Leakage Detection System In Water Cooled Generator Stator Windings", EPRI Workshop, Atlanta, GA, Maintaining The Integrity of Water– Cooled Generator Stator Windings, held Jun., 1995, pp. 1–20.

(List continued on next page.)

*Primary Examiner*—Safet Metjahic
*Assistant Examiner*—James C Kerveros
(74) *Attorney, Agent, or Firm*—Robert P. Santandrea; Noreen C. Johnson (57) ABSTRACT

A stray field electrode (1) includes a base material (2) and a conductive filler material (3). The base material is preferably an insulating material, such as a silicone elastomer film. The conductive filler material is preferably a metal, such as silver particles dispersed in the silicone elastomer film. A set of stray field electrodes (16, 17, 18) may be used to determine the presence of water in a material (8), such as electrical generator insulation (14), by comparing a phase angle for the electric field (19, 20) between the electrodes with a predetermined phase angle for a dry material (8).

34 Claims, 5 Drawing Sheets

U.S. PATENT DOCUMENTS

| | | | |
|---|---|---|---|
| 4,429,343 | * | 1/1984 | Freud .................................. 361/286 |
| 4,522,060 | | 6/1985 | Murata et al. . |
| 4,588,943 | | 5/1986 | Hirth . |
| 4,675,596 | * | 6/1987 | Smith .................................. 324/683 |
| 4,806,212 | | 2/1989 | Wessling et al. . |
| 4,845,421 | | 7/1989 | Howarth et al. . |
| 5,134,380 | * | 7/1992 | Jonas .................................. 324/674 |
| 5,283,711 | | 2/1994 | Schmitz .............................. 361/286 |
| 5,345,821 | | 9/1994 | Reich et al. ...................... 73/335.04 |
| 5,442,293 | | 8/1995 | Lange .................................. 324/332 |
| 5,859,536 | * | 1/1999 | Stockton ............................ 324/664 |
| 6,114,863 | * | 9/2000 | Krahn et al. ....................... 324/664 |

OTHER PUBLICATIONS

JE Timperley, "Capacitance Mapping Of A Series Connection With An Active Water Leak", Rotating Machinery, Doble Engineering Company, 62PA1C95, 1995, pp. 7–5.113 7–5.5 and "Discussion of James E. Timperley Paper", 7–5A.1—7–5A.3. Missing Month.

H. Gonishi et al., "Developmeny of New Diagnostic Method For Hot–Line XLPE Cables With Water Trees", IEEE Transactions on Power Delivery, vol. PWRD–2, No. 1, Jan. 1987.

"Inspection of Generators with Water Cooled Stator Windings", General Electric Technical Information Letter, GE Power Generation, TIL 1098–3R2, Jan. 24, 1995, pp. 1–8.

NV Afanas'ev et al., "The Effect of Film Water On The Dielectric Properties of Mica—Part I", from Researchy In Surface Forces, vol. 2, pp. 176–180, NV Derjaguin, Ed. (1966), Consultants Bureau, NY. Missing Month.

*Concise Encyclopedia of Polymer Science & Engineering*, John Wiley & Sons 1990, 1998, pp. 1056–1058. Missing Month.

"Structure of Water Near Solid Interfaces," Industrial & Engineering Chemistry, vol. 61, No. 11, Nov. 1969, pp. 10–47.

"Motions & Relaxations of Confined Liquids," by S. Granick in Science, vol. 253, Sep. 1991, pp. 1374–1379. Missing Month.

Kirk–Othmer Encyclopedia of Chemical Technology, $3^{rd}$ Edition, vol. 18, (1982). Missing Month.

Derwent Abstract AN 93–204433, Jun. 30, 1992.

European Search Report for EP 99 30 3235 corresponding to U.S. Ser. No. 09/069,448.

Article Entitled "New materials for electrochemical sensingI.Rigid conducting composites" trends in analytical chemistry, vol. 15, No. 7, 1996—F. Cespedes, E. Martinez–Fabregas, S. Alegret, Bellaterra, Spain. No Month Date.

* cited by examiner

MATERIAL FOR IMPROVED SENSITIVITY OF STRAY FIELD ELECTRODES

This application is a continuation-in-part of U.S. Ser. No. 09/069,448, filed Apr. 29, 1998, and now U.S. Pat. No 6,114,863 which is hereby incorporated by reference in its entirety.

BACKGROUND OF THE INVENTION

This invention relates generally to composite stray field electrode materials. More particularly, it relates to stray field electrodes comprising filled conductive silicone elastomers and to methods for determining the presence of water in insulating materials, such as those used in electrical power generation.

Water detection methods are available for a variety of end use applications. For example, the water content of porous materials such as soil has been measured by using electromagnetic fields, as described in U.S. Pat. No. 5,442,293. Moreover, the determination of moisture content in materials such as wet or cured concrete is sometimes very important in the building industry. U.S. Pat. No. 3,870,951, for example, describes an electrical measuring probe useful for such a purpose.

Water detection is also important in water-cooled electrical generators. The stator yoke in these generators surrounds the armature core and partially encloses the armature windings, which are sometimes referred to as "stator winding" or "stator bar." As one typical example, copper conductors are usually wound in the armature to form loops. The armature windings are arranged in such a manner that the desired voltage and current characteristics can be maintained by the generator in operation. A number of the individual conductors (sometimes referred to herein as "strands") inside the stator bars are hollow, to allow for the flow of cooling water from a coolant system.

Electrical insulation is wrapped around both the strands and the stator bars, and is also often used to separate some of the strands from each other, or from other conductive structures, such as portions of the steel stator yoke. The ground wall insulation which is usually wrapped around the stator bars can be formed of various materials. Examples are fiberglass tape, vacuum/pressure-impregnating resins, casting and potting resins, and different types of laminates made by bonding layers of a reinforcing web.

A preferred type of generator insulation is mica-based insulating tapes. Various types of mica-based tapes are available (e.g., Micapal™ tapes). Most of these types consist of mica flakes or laminates bound together with a resinous binder, such as an epoxy material.

The durability and integrity of the insulation during operation of electrical generators is of great importance. The stator bars operate at very high voltages, e.g., greater than 10,000 volts in a large generator. The voltage must remain isolated from ground. Any "flashover" from one stator bar to another, or from one electrical phase to another, or to ground could activate safety mechanisms which automatically shut down the generator. A sudden shut-down could instantaneously direct the current flow (often greater than 2,000 amps) to ground, an event which in some circumstances could severely damage many of the generator components.

The leakage of water into the ground-wall insulation can damage water-cooled electric generators and ultimately lead to the catastrophic failures mentioned above. Water leaks from the coolant system are often found in or near the many brazed connections at the junction of a stator winding terminus and a water hose connection. The leaks are caused by a variety of factors, such as stress cracks or porosity in copper castings or corrosion of the braze materials. As described by J. Timperley in *Rotating Machinery*, 62 PAIC 95 (copyright 1995 Doble Engineering Co.), water can then begin migrating along voids between the ground wall insulation and the strands, and can delaminate the mica-flake tape layers within the ground wall insulation. Failure of the generator can occur when water contaminates the ground-wall insulation in the vicinity of the stator core, where higher voltage stresses are present. Although on-line failures of generators due to water leakage are a rare occurrence, the damage caused by such an event could be extreme, as mentioned above.

Failure is most often experienced during routine maintenance or testing of the generator. For example, a stator water pumping unit may be left in operation when the generator is degassed. Under those conditions, the pressure differential may force water through a leak site and into the ground-wall insulation. In general, even very small water leaks can be detrimental to a generator if they are allowed to persist.

There are a number of techniques which are presently used to detect water in electrical insulation. One technique is capacitance mapping, as described in the Timperley article mentioned above. Another technique is the so-called direct current ("DC") technique for detecting water "trees" in insulated power cables, described in H. Oonishi et al. in IEEE Transactions on Power Delivery, Vol. PWRD-2, No. 1, January 1987. Other techniques also include the stator leak monitoring system (SLMS), use of a tracer gas such as sulfur hexafluoride, or the use of thermographic video cameras.

However, all of the above techniques suffer from one or more disadvantages. The disadvantages include poor sensitivity to the presence of water, inability to detect water while the generator is on-line, failure to accurately indicate the location of the water in the insulation, and damage to the insulation being monitored.

Thus, a method and an apparatus for detecting the presence of water in materials which overcomes or reduces these disadvantages would be desirable. It is desirable that an electrode, method and apparatus be suitable for testing of an insulating material which is incorporated into electrical power equipment, such as water-cooled generator insulation. It would be desirable if the apparatus could be employed while the power equipment was in operation, so that unnecessary shut-downs could be avoided. Finally, the method and apparatus should be accurate, exhibit good sensitivity to the presence of water and not add significant expense to any of the related procedures, such as power generation. The present invention is directed to overcoming or at least reducing one or more problems set forth above.

BRIEF SUMMARY OF THE INVENTION

In accordance with one aspect of the present invention, there is provided an electrode comprising a base material and a conductive filler material. In a preferred embodiment, the electrode comprises a stray field electrode, the base material comprises an insulating material, such as a silicone elastomer, and the conductive filler comprises at least one metal or carbon black.

In accordance with another aspect of the present invention there is provided a method for determining a presence of water in a first material, comprising:

(a) placing a set of electrodes, comprising an insulating base material and a conductive filler material, on a surface of the first material;

(b) establishing an electric field between the electrodes;

(c) measuring a phase angle for the electric field at one or more selected frequencies; and (d) comparing the measured phase angle value to a predetermined phase angle value corresponding to dry first material, wherein a significant difference between the measured phase angle value and the predetermined phase angle value is indicative of the presence of water in the first material.

In accordance with another aspect of the present invention there is provided an electrical generator, comprising:

(a) an insulating material surrounding at least a portion of an electrically conductive component of the generator;

(b) at least one set of composite stray field electrodes, comprising an insulating base material and a conductive filler material, located on a surface of a first portion of the insulating material;

(c) a power source connected to said at least one set of composite stray field electrodes which permits an establishment of an electrical field between the electrodes;

(d) a phase analyzer for measuring a phase angle associated with the electrical field at one or more selected frequencies; and (e) means for comparing a known phase angle value corresponding to dry insulating material to the measured phase angle value, and for providing an indication of whether water is present in the first portion of the insulating material based on the comparison of the phase angle values.

DETAILED DESCRIPTION OF THE INVENTION

U.S. patent application Ser. No. 09/069,448, filed on Apr. 29, 1998 titled "A Method For Determining The Presence Of Water in Materials," naming John R. Krahn and Clive Reed as co-inventors is incorporated herein by reference in its entirety. The method described in the above mentioned application is employed to determine the presence of water in a variety of materials. The water detection method is based on the discovery that the measured value of the phase angle for an electric field established between two stray field electrodes placed on the material being monitored is affected by the presence of water in the material. The stray field electrodes are used to determine the presence of water in a material, such as electrical generator insulation, by comparing the measured phase angle value for the electric field between the electrodes with a predetermined phase angle value for a dry material.

The above mentioned application discloses using conductive stray field electrodes in the method of determining whether water is present in the material being monitored. The preferred electrode material in the above mentioned application was a metal, such as copper. However, while copper stray field electrodes provide a reliable indication of the presence of water in the material being monitored, the measured signal may be improved. Therefore, a measured differential phase angle signal stronger than the signal produced by an electric field generated by the copper electrodes would be desirable. Furthermore, when the thin copper stray field electrodes are used to measure the water content of a rough surface, such as insulation surrounding generator stator bars, the electrodes may become irreversibly deformed due to the contact with the rough surface. Therefore, it would be desirable to obtain a resilient and compliant electrode material which will not become deformed after being placed in contact with a rough surface and which generates an electric field that produces a strong measured differential phase angle signal.

The present inventor has discovered that composite stray field electrodes unexpectedly offer a stronger measured differential phase angle signal than the more conductive single component metallic (i.e., copper or other metal) electrodes during monitoring for the presence of water in insulating materials, such as insulation on generator stator bars.

The composite stray field electrode comprises a base material and a conductive filler material. In one embodiment, the base material comprises an insulating material and the conductive filler material comprises at least one metal. In another embodiment, the base material comprises a conductive material, such as a conductive polymer material, and the conductive filler material comprises at least one metal.

Figure 1:
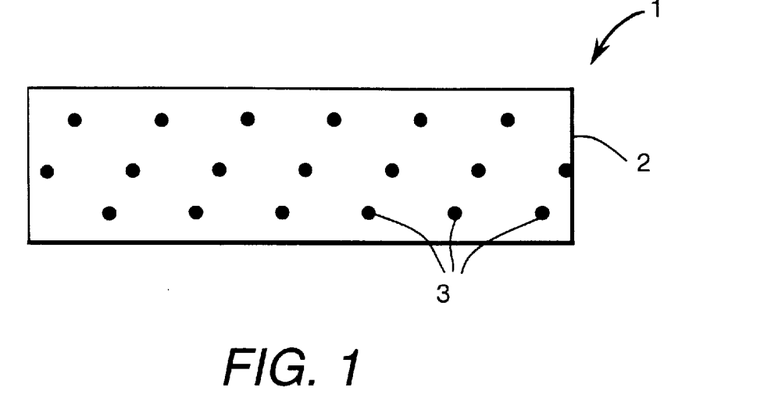
FIGS. 1, 2 and 3 are cross-sectional views of electrodes according to embodiments of the present invention.
Figure 2:
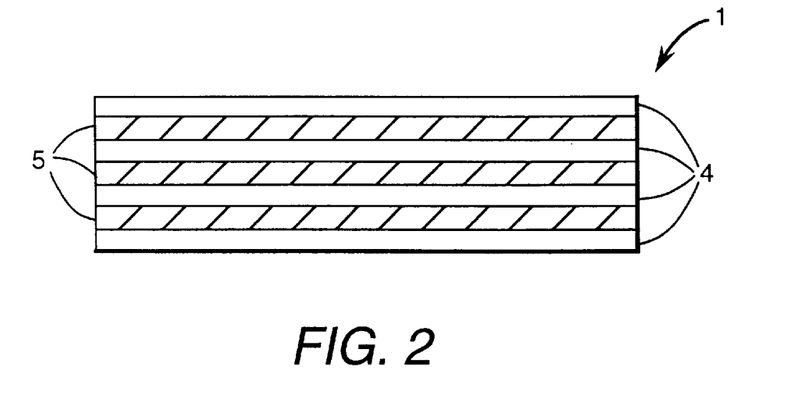
Figure 3:
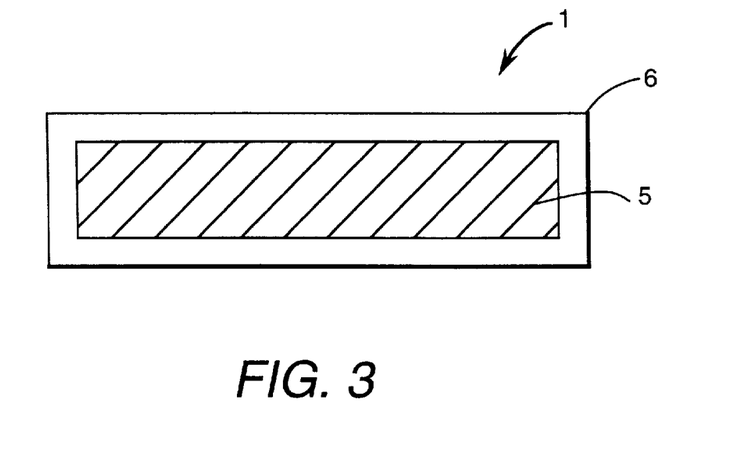

FIGS. 1, 2 and 3 show several examples of how the base material and the conductive filler material may be shaped into a composite electrode 1. The present invention should not be considered to be limited to these examples, which are shown for the purpose of illustrating the preferred embodiments of the invention. Referring to FIG. 1, the base material may comprise a thin film 2 and the conductive filler material may comprise discrete metal particles 3 dispersed throughout the film 2. Alternatively, both the base material and the conductive filler material may comprise a plurality of laminated thin films or foils. For example, in FIG. 2, the base material films 4 and the conductive filler films 5 are layered over each other. The thickness and number of each kind of film may be chosen according to a desired result. In another embodiment of the present invention, the base material comprises a vessel 6 which encloses the conductive filler film 5, as shown in FIG. 3. Alternatively, the vessel 6 may contain the laminate of base material films 4 and conductive filler films 5 shown in FIG. 2.

The base material may comprise any insulating material, such as elastomers, rubbers, plastics, polymers, ceramics, glasses, oxide, nitrate, silicate or carbonate compounds, clays, micas, cellulosic materials, as well as composites and combinations of the above materials. The conductive filler material may comprise any conductive material, such as at least one of silver, nickel, aluminum, copper, gold, silver plated copper, silver plated aluminum, silver plated nickel, silver plated glass, nickel graphite and alloys thereof. A non-limiting example of a non-metal conductive filler is carbon black filler in a polymer based base material.

It should be noted that some categories of materials mentioned above are not mutually exclusive. For example, plastics are materials that can be shaped by flow and often comprise organic polymers or resins. However, plastics may also comprise additives and reinforcing filler materials in addition to the polymer material. Non-limiting examples of plastics that may be used as the electrode base material are PTFE and polyvinyl carbazole.

Rubbers and elastomers are also based on polymers, but have a lower stiffness and reversible elasticity usually not found in plastics. Furthermore, the terms rubber and elastomer are sometimes used interchangeably. The term elastomer includes any natural or synthetic material that exhibits high extensibility and flexibility, while the term rubber includes any natural or synthetic thermoset or thermoplastic elastomeric materials.

The preferred base material of the composite stray field electrode is a rubber or an elastomer. These resilient materials exhibit long range deformability on the application of stress and complete recovery on the removal of stress. Therefore these materials have an ability to closely conform to a rough testing surfaces, such as generator stator insulation, and the ability to resist damage by the rough testing surface. Furthermore, elastomers which can be cured after being applied to the testing surface may be advantageous in some aspects of the present invention because they have the ability to assume the contour of the testing surface. Non limiting examples of rubbers or elastomers that may be used as the base material of the stray field electrode are styrene butadiene, nitrile, ethylene propylene, polybutadiene, polyisoprene and butyl.

The most preferred base materials are silicone elastomers, such as cross-linking polyorganosiloxanes or polyorganosiloxane rubbers. Non limiting examples of polyorganosiloxanes are polydimethylsiloxanes ("PDMS") having the formula:

where R is a hydrogen, an organic radical or a silyl radical containing one or more reactive groups, such as vinyl or alkoxy, and x is preferably 200 to 11,000, as described in the *Concise Encyclopedia of Polymer Science and Engineering*, John Wiley & Sons 1990, 1998, pages 1056 to 1058, incorporated herein by reference. The elastomer may also comprise a copolymer in which 5 to 15% of the methyl groups are replaced with phenyl groups. The silicone elastomers may comprise room temperature vulcanized elastomers or elastomers that are vulcanized above room temperature (also known as heat cured rubbers). The silicone elastomers may also contain additives such as antioxidants, adhesion promoters and reinforcing fillers.

In a preferred aspect of the present invention, the electrode 1 base material comprises a PDMS elastomer film 2 and the conductive filler material comprises silver power particles 3 dispersed throughout film 2, as shown in FIG. 1. The silicone elastomers in general, and the PDMS elastomers in particular, may be manufactured by any known method, such as the methods disclosed on pages 1056 to 1058 of the *Concise Encyclopedia of Polymer Science and Engineering*, John Wiley & Sons 1990, 1998, incorporated herein by reference. For example, PDMS may be produced by heating dimethylsilicone gum with an organic peroxide, such as benzoyl peroxide, to crosslink the gum, followed by dispersing conductive filler particles, such as silver particles, into the elastomer by grinding or milling in the presence of a solvent.

While not wishing to be bound by any particular theory, the present inventor theorizes that the improved differential phase angle signal due to a field generated by the composite electrodes compared to that from the copper electrodes may be due to the following effect. The present inventor believes that the stray electric field is distributed differently between the composite electrodes than between the copper electrodes. The particular distribution of the electric field between the composite stray field electrodes probably couples with any conductor present adjacent to the insulating material being monitored. For example, if a generator stator insulation is being monitored, the electric field emitted by the composite stray field electrodes probably couples with the conductor plane inside the stator bar. However, it is believed that the electric field between the copper electrodes probably does not couple with the conductor plane or couples to a lesser extent than the electric field between the composite electrodes.

Figure 4:
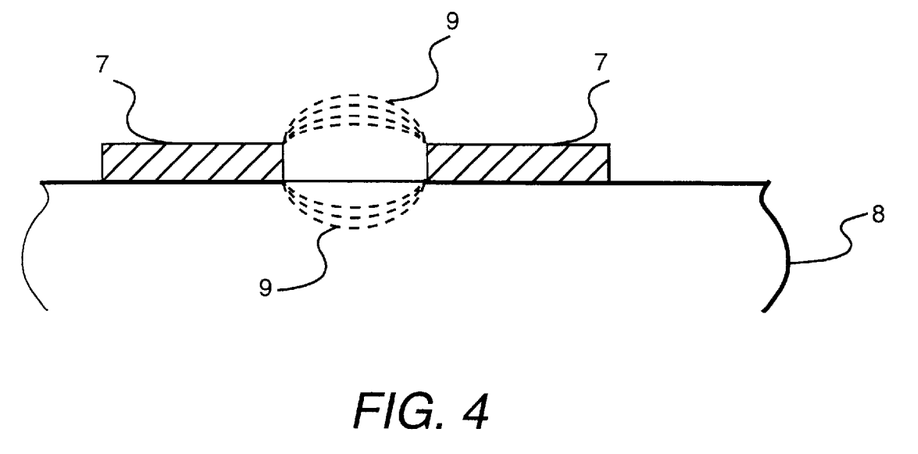
FIGS. 4 and 5 are cross-sectional views of metal and composite stray field electrodes for generating an electric field.
Figure 5:
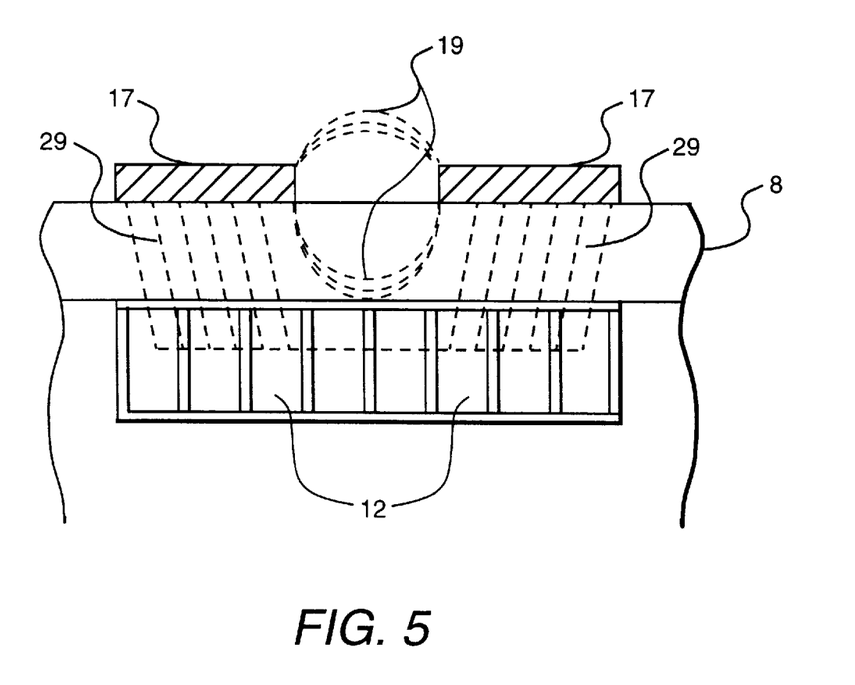

Consequently, as shown in FIG. 4, the electric field 9 (illustrated in phantom) generated by the copper electrodes 7 is probably directed less deeply into the insulating material 8 being monitored. However, the electric field 19 generated by the composite electrodes 17 is probably directed preferentially into and/or through the insulating layer 8 being monitored, as shown in FIG. 5. Furthermore, the capacitively coupled electric field 29 is probably directed between the electrodes 17 roughly horizontally through the collective copper strand 12 bundle and roughly vertically through the insulating layer 8. The electric field 19, 29 generated by the composite electrodes 17 probes more of the insulating material 8 by extending deeper into material 8, thus providing a stronger measured signal for a given amount of water present in material 8. It should be noted that the field lines 9, 19, 29 illustrated in FIGS. 4 and 5 are shown to illustrate the above described theory, and are not intended to represent the path of actual field lines.

Figure 6:
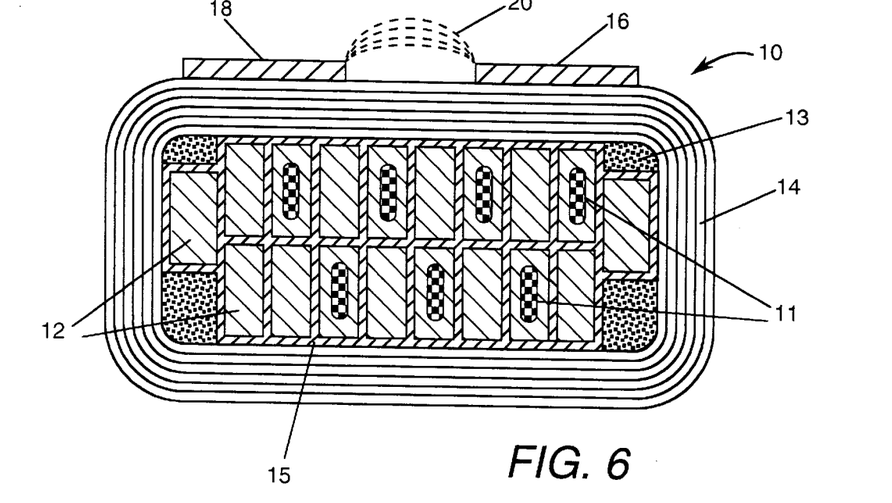
FIG. 6 is a cross-sectional view of a stator component of a water-cooled electrical generator.

FIG. 6 is a cross-sectional view of a typical stator component 10 for a water-cooled electrical generator. The stator includes stationary conductors or strands 12, often made of copper. The strands in the central portion of the figure are electrically-insulated from each other by an enamel material 15, while the strands at each end are surrounded by transposition putty material 13. For this type of generator, some or all of the strands 12 may be hollow, as shown by hollow spaces 11, to allow the passage of water to and from the coolant system, as described above. (Electrical generators are well-known in the art and described in many references).

The collective strand bundle is surrounded by multiple layers of electrical insulation 14, i.e., ground wall insulation. The number of insulation layers and their particular arrangement is not critical, and depend on design specifications for the generator. Often, the insulation layers are made from mica-based materials which include a binder. Initially, the mica layers are flexible enough to be wound or wrapped around the strands, but, after curing, the mica layers are relatively hard.

The composite stray field electrodes 16 and 18 described above are placed on an outside surface of insulation 14. The shape and size of the electrodes are not critical to this invention, as long as an electric field 20 (illustrated in phantom) can be generated between them. A particular voltage for the electrical field is also not especially important, and depends in part on which voltage measurements will allow for the most convenient readings of phase angle and frequency, as further discussed below. In general, the voltage is usually in the range of about 100 millivolts to about 10 volts, more frequently between about 100 millivolts and 2 volts and most frequently, between about 0.5 volt and 1 volt.

Figures 7, 8:
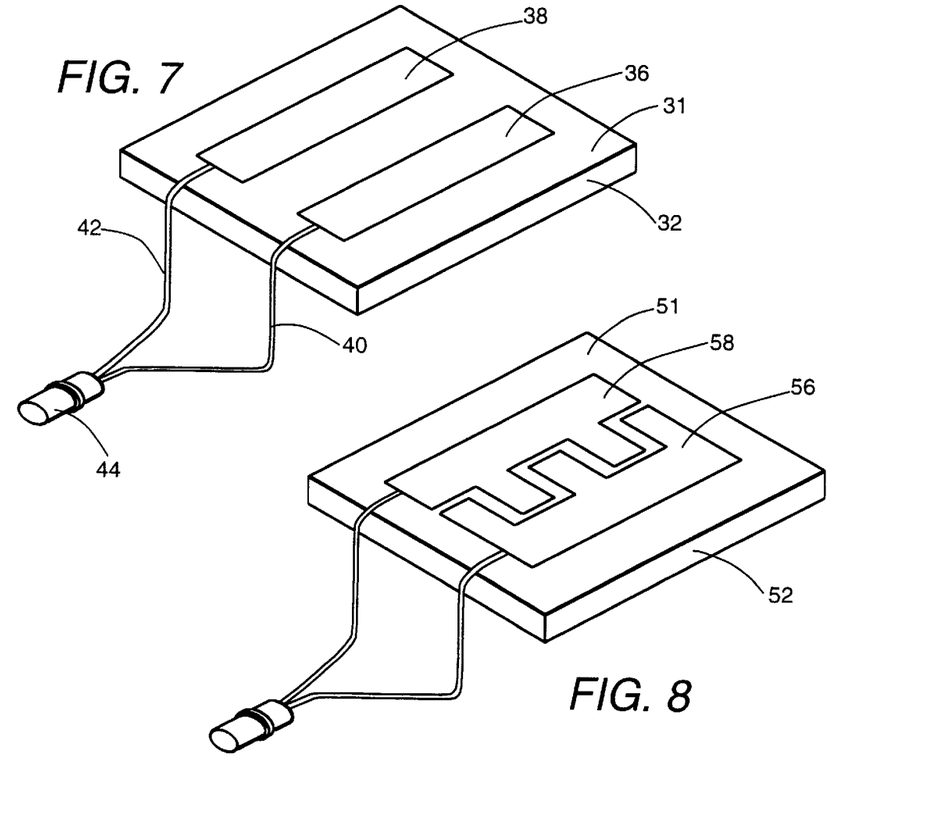
FIG. 7 is top view of a set of electrodes in place on the surface of an insulator layer, according to one embodiment of this invention.
FIG. 8 is top view of a set of electrodes in place on the surface of an insulator layer, according to an alternative embodiment of this invention.

FIG. 7 is top view of a set of composite stray field electrodes 36, 38 in place on the surface 31 of an insulator 32, which could represent one or more of the insulation layers depicted in FIG. 6. In this embodiment, each electrode is substantially rectangular, and parallel to the other electrode. The dimensions of the electrodes are not particularly critical, and are dictated in part by the durability of the electrode material and the size of the material being monitored.

The separation between the electrodes will depend in part on the thickness of the material being monitored. A greater separation allows for greater penetration of the electric field into the depth of the material, although the strength of the field may have to be increased to achieve desired sensitivity. In general, the distance between the electrodes will range from about 0.1 cm to about 3.0 cm, and preferably from about 0.5 cm to about 2 cm or from about 0.5 cm to 1.5 cm, most preferably about 1.5 cm. For a layer of material having a thickness of about 0.4 cm to about 0.8 cm, the distance between the electrodes is usually in the range of about 0.8 cm to about 1.2 cm. For a thicker material, the distance may be greater, such as about 1.2 cm to about 1.7 cm.

Each electrode may be attached to a wire or lead 40, 42. The leads may in turn be fitted into a connector 44, such as a BNC fitting, and then routed to an appropriate power supply. The power supply is usually part of a phase analyzer device, as described below.

FIG. 8 is top view of an alternative set of composite electrodes 56, 58 in place on the surface 51 of an insulator layer 52. In this embodiment, the electrodes are still separated from each other, but interdigitated. Such an arrangement is preferred in some embodiments because it permits the establishment of an electric field over a greater amount of surface area in a particular section of the material being monitored. The apart spacing for this set of electrodes may be the same as described above. Moreover, other arrangements of electrodes are also possible. For example, they could be situated in a concentric arrangement, which would also permit the monitoring of a considerable surface area of material. Those skilled in the art will be able to readily evaluate different arrangements for the electrodes for a give type and shape of material being examined for water content, based on the teachings herein.

If necessary for stability, the composite electrodes may be affixed to the surface of the material being monitored. Any technique may be used to affix the electrodes, as long as it does not interfere with their ability to maintain the electric field. Examples include the use of adhesives, an air pressure pad, or mechanical means, such as alligator clips or brackets. The electrodes should be easily detachable from the surface if their position on the surface is to be frequently changed.

The electrical phase angle is a known measurement for an electric field having a given frequency. Phase analyzers are commercially available from various manufacturers, such as Hewlett-Packard. The phase analyzer can easily be connected to the electrodes through the BNC fitting 44.

The most appropriate frequency for carrying out this invention is that which is most sensitive to the presence of water in a particular material being monitored. It can be determined without undue effort by testing trial samples of the material. Usually, the frequency at which the phase angle will be measured is in the range of about 75 kHz to about 3 MHz, but it could extend to as low as about 10 kHz, or as high as about 100 MHz. The preferred range for composite electrodes is below 1 MHz, preferably from about 100 kHz to about 300 kHz. The composite electrodes produce up to a 28% improvement in the strength of the detected signal compared to the strength of the signal detected from identically shaped metal (i.e., copper) electrodes in the 100 kHz to 300 kHz frequency range for a given amount of water. The improvement in signal strength, however, is broad, spanning the entire 10 kHz to 10 MHz range.

When the most appropriate frequency has been established, the phase angle can be measured for a material free of water, at that particular frequency. A significant change in that phase angle value for a test material will indicate the presence of bound water in the test material, due in part to the change in relaxation time for water molecules within the material being monitored. As the water content increases, the strength of the "relaxation signal" may also increase, as evidenced by a greater change in the phase angle value. The general concepts of bound water and relaxation are discussed in the following articles: "Structure of Water Near Solid Interfaces," Industrial and Engineering Chemistry, Vol. 61, No. 11, November 1969, pp. 10–47, and "Motions and Relaxations of Combined Liquids," by S. Granick in Science, Col. 253, September 1991, pp. 1374–1379, respectively. Both are incorporated herein by reference in their entirety.

A "significant change" in the phase angle will depend in part on the type of material being monitored, and the depth of water within a layer of the material. Usually, a variation of phase angle of about 0.3 degrees or more (i.e., a variation from the phase angle value for the material in its dry state) is a reliable indication that water is present in the material. As an illustration, a typical phase angle value (within the frequency range stated above) for a dry portion of an inorganic-based insulating material is often about (minus) −89.5 degrees. A reading of −89.4 or −89.3 degrees for a test sample of the material is still considered to be indicative of a dry material, while a reading of about −89.2 degrees is a good indication that water may be present in the sample. Readings of less than about −89.2 degrees reliably confirm the presence of water. There may sometimes be slight variations for phase angle values for a given sample, due in part to minor electrical fluctuations related to the equipment being used. However, the average of repeated readings confirms that any deviation is usually insignificant. In addition to the phase analyzer, a computer or a similar data processing circuit or apparatus may be used to analyze the detected or measured phase angle signal, to compare the detected or measured signal to the predetermined phase angle signal indicative of a dry material being monitored, and to output a result indicative of the presence or absence of water in the insulating material being monitored. Alternatively, the phase analyzer may be operated to output a result indicative of the presence or absence of water in the insulating material being monitored.

The present process can be used to detect water to a depth of up to about 1.5 cm within a layer (or through multiple layers) of material, such as mica- or cellulose-based insulation. Usually, the depth at which water is detected is in the range of about 0.5 cm to about 1.0 cm. As mentioned above, the spacing of the electrodes, as well as the strength of the electric field, can be varied to test for water at different depths. Usually if the water content increases at a given depth, the phase angle value exhibits a greater change, as discussed above. If the water content remains constant, but its depth within the layer of material increases, the relaxation signal tends to decrease, as signified by a smaller change in the phase angle value.

Sometimes, the most appropriate electrical frequency to be used for testing a given type of material is not known. In that instance, it can be determined by carrying out a frequency sweep for the electrical field established between the electrodes. The frequency sweep establishes a plot of the electrical phase angle as a function of the frequency being generated. It can readily be measured by the use of a device which measures these types of field properties, such as an impedance/gain-phase analyzer. In the examples which follow, a frequency sweep is undertaken as the sample is tested for the presence of water.

It should be apparent that the presently-described process would be very useful for monitoring the presence of water in or around electrical components, especially electrical generator components, such as stator bar insulation 14 shown in FIG. 6, as well as insulation around other generator components. In view of the fact that direct current and alternating-current (AC) generators are well-known, an extensive description of them is not necessary here. (See, for example, the Encyclopedia Americana, International Edition, Volume 12, copyright 1964, pp. 378–385, the contents of which are incorporated herein by reference). The primary components of a DC generator are the armature, the field poles, brushes, brush rigging, commutator, frame (or "yoke"), and end frames or end bells. In an AC generator, the stationary conductors (armature coils) are held in place in slots in a frame assembly (stator), as alluded to earlier. The assembly that supports the field coils and rotating poles is referred to as the "rotor."

Insulating materials may sometimes be used to separate or encapsulate the principal components mentioned above, as well as various other components, such as interpoles, compensating windings, and devices or controls which regulate the generated voltage and current output. Water from any outside source which seeps into the insulation or penetrates it in some other manner may be of great concern. Moreover, water which originates in the cooling system of a water-cooled generator and migrates into the insulation can also represent a serious problem. The process described herein effectively addresses these concerns. The present invention may be used to detect the presence of deionized water, which is often used for cooling systems, or regular tap water.

Multiple sets of electrodes could be placed on the surface of the insulating material, e.g., on the surface of insulating material which surrounds stator bars in a water-cooled generator. Each set of electrodes could be connected to its own power source and phase analyzer. Alternatively, all of the sets could be connected to a central power source and phase analyzer, via a circuit pathway which could be readily designed by those skilled in the art. In this manner, many different sites on the insulation can be simultaneously monitored for the presence of water. An additional attribute of this invention is that the presence of electrical conductors (e.g., copper windings) in the vicinity of the electrodes and the electrical field does not adversely affect phase angle measurements for the process.

The effect of the present invention is not limited to monitoring of the insulation on generator components as described above. Other suitable materials with which water molecules interact may be monitored using the composite stray field electrodes.

Non-limiting examples of materials which can be monitored are cellulosic materials such as paper; inorganic materials like those based on mica or industrial clays; inorganic oxides, e.g., metal oxides; glass-based materials, e.g., glass fibers; organic polymers; and various combinations of any of these materials. Examples of multi-component materials are mica or glass fiber sheets held together with resinous binder materials. As another example, organic polymers and other base materials are frequently mixed with various fibers or reinforcing agents, such as titanium dioxide, metal carbonates (e.g., calcium carbonate), metal silicates, barium sulfate, and clays.

Some specific examples of metal oxides are magnesium oxide, aluminum oxide, zinc oxide, and zirconium oxide. Specific examples of organic polymer materials are polyesters, polyamides, polystyrenes which have hydrophilic characteristics (e.g., polyhydroxystyrenes), polyethers, polyimides, silicones (i.e., those which contain water-interactive fillers such as aluminum trihydrate); rubber-based polymers; epoxies, phenolics, acrylics, polyurethanes, mixtures of any of the foregoing; and copolymers of any of the foregoing.

Preferably, the electrically insulating materials being monitored using the compound electrodes are located adjacent to conductive material. The electrodes of the present invention are especially useful for monitoring electrical insulators surrounding conductive electrical components. Several specific examples of electrical insulation include the mica-based materials discussed above (commercially available under trade names such as Micapal™ and Mica-Flex™); alumina-based materials, glass fiber-based materials; and a variety of composite materials, such as those based on laminations of cellulose, glass, asbestos, and/or synthetic fibers, bonded together with resins and then cured. In use, the insulating material is usually in the form of a tape or layer, which can be pre-shaped to surround any component being protected.

Multiple layers are sometimes used, e.g., layers of mica-based tape, for a total thickness between about 1 mm and about 10 mm.

The following examples are merely illustrative, and should not be construed to be any sort of limitation on the scope of the claimed invention.

EXAMPLE 1

This example illustrates the impedance of the composite electrodes. Three sets of two composite silicone elastomer film strips filled with dispersed silver and silver coated copper powder particles were used as electrodes in this experiment. The strips were placed in a position parallel to each other (along their length), 1.5 cm apart, on a surface of a mica-based tape. The electrodes were secured to the tape by alligator clips.

Each set of the electrodes were manufactured by Specialty Silicone Products, Inc. ("SSP") of Ballston Spa, New York, U.S.A. The first set of electrodes comprised the SSP-1729A&B (product number) PDMS elastomer with a metal filler. The second set comprised the SSP-1510 SPC PDMS elastomer with a metal filler. The third set comprised the SSP-547-65 PDMS elastomer with a metal filler. For example, the SSP-1510 series of elastomers are "form-in-place" elastomers that may be vulcanized after being formed in a preferred location. The SSP-547-65 elastomer contains silver plated copper particles having a volume resistivity of 0.006 and Shore A hardness of 65.

Each electrode was connected with leads to a BNC fitting. The BNC fitting was in turn connected to an HP4194A impedance/gain-phase analyzer with an HP54003 50 Ohm impedance probe. An electric field was established between each set of the electrodes. In each instance, the impedance at a frequency of 100 to 104 kHz was measured and recorded.

Figure 9:
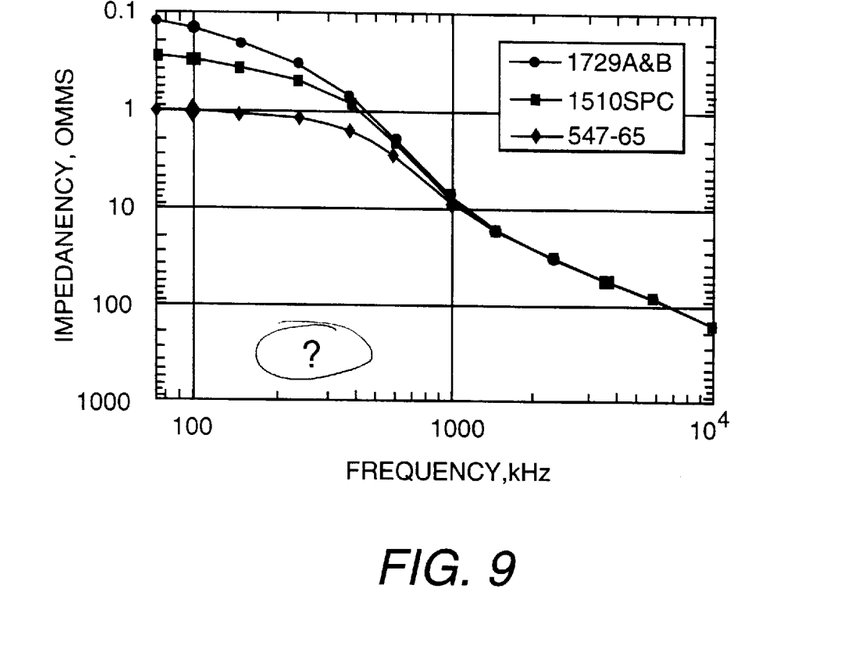
FIG. 9 is a plot of impedance values as a function of frequency for various composite electrode materials according to an exemplary embodiment of the present invention.

The results are shown in FIG. 9. Each composite silicone elastomer electrode had a satisfactory impedance of between about 0.1 and about 100 ohms over the entire frequency range.

EXAMPLE 2

Figure 10:
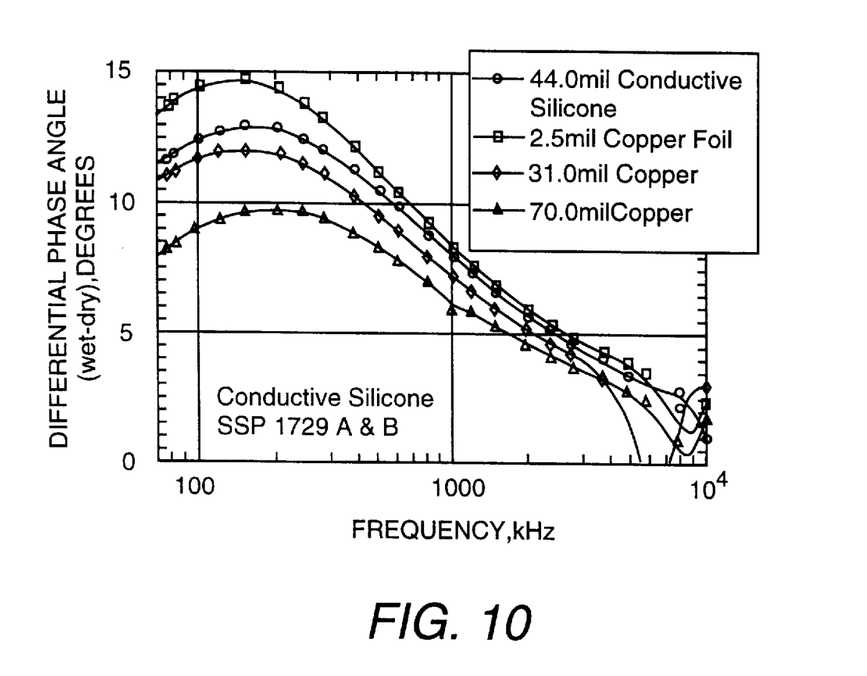
FIGS. 10 and 11 are plots of electrical phase angle values as a function of frequency for materials being monitored according to an exemplary embodiment of the present invention.

This example illustrates the improvement in the measured or detected phase angle signal arising from the use of the composite electrodes. FIG. 10 is a plot of differential electrical phase angle values as a function of frequency for different electrodes. Differential phase angle means the difference between the measured phase angle for the material being monitored and the predetermined phase angle for the dry material, using the same electrodes.

As may be seen from FIG. 10, a 44 mil thick SSP-1729A&B conductive silicone elastomer electrode set (square markers) produced a significantly stronger signal than any of the three copper electrode sets (circle, triangle and rhombus markers). The signal increased as the copper electrode thickness decreased. However, the 44 mil elastomer electrode set produced a stronger signal than the much thinner 2.5 mil copper foil electrode set (circle markers). Therefore, the use of the composite electrode according to an embodiment of the present invention allows the use of a material that is more resistant to damage and deformation and that produces a stronger measured signal than copper electrodes. The improvement in signal strength was evident over the entire frequency range, but was especially pronounced in the preferred about 100 kHz to about 300 kHz frequency range.

EXAMPLE 3

Figure 11:
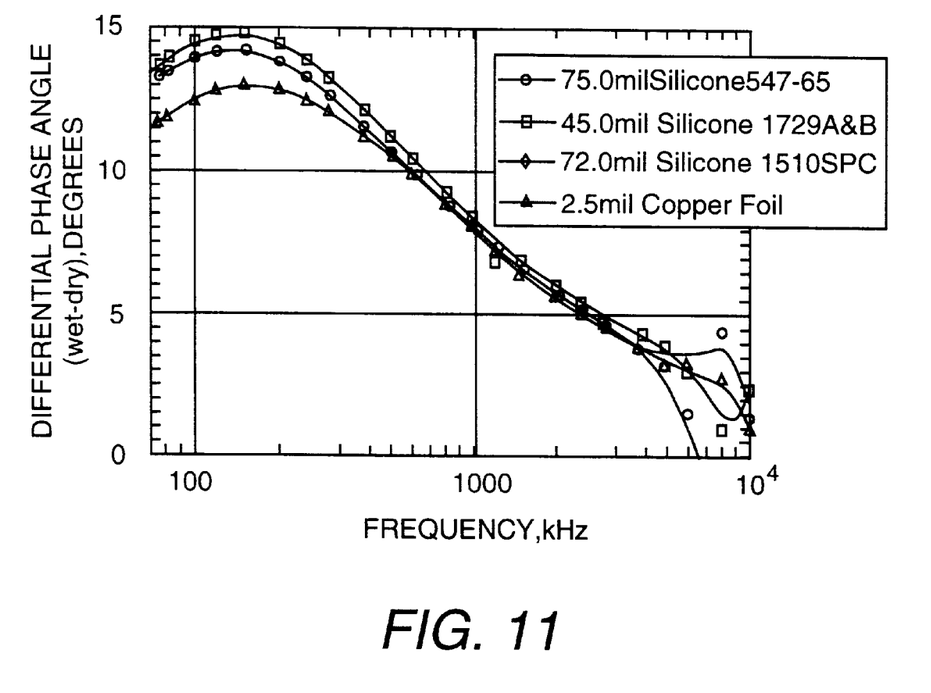

This example illustrates the improvement in the measured or detected phase angle signal arising from decreasing the thickness of the composite electrodes. As may be seen from FIG. 11, the measured or detected signal is stronger from a 45 mil silicone elastomer composite electrodes (square markers) than from 75 or 72 mil silicone elastomer electrodes (circle and rhombus markers). Therefore, the elastomer electrode is preferably about 45 mil or less. The measured signal from the 75 or 72 mil silicone elastomer composite electrodes is larger than from a much thinner 2.5 mil copper foil electrodes (triangle markers).

Furthermore, the strength of the signal is apparently not a function of the elastomer composition. As may be seen in FIG. 11, the strength of the signal is about the same from SSP-547-65 (circle markers) and SSP-1510SPC (rhombus markers) silicone elastomer electrodes of the same thickness. Therefore, the scope of the invention includes any composite electrode, preferably comprising a silicone elastomer base and a metal filler.

The preferred embodiments have been set forth herein for the purpose of illustration. However, this description should not be deemed to be a limitation on the scope of the invention. Accordingly, various modifications, adaptations, and alternatives may occur to one skilled in the art without departing from the spirit and scope of the claimed inventive concept.

All of the patents, patent applications, articles, and texts which are mentioned above are incorporated herein by reference.

What is claimed is:

1. An electrode comprising:
    a pair of discrete electrodes, each one of the electrodes being disposable on a solid insulating material and comprising
    a base material; and
    a conductive filler material comprising a plurality of discrete conductive particles dispersed throughout the base material; and
    a phase analyzer which receives a signal from the electrodes, wherein the phase analyzer measures a phase angle of an electric field between the electrodes.

2. The apparatus of claim 1, wherein:
    the at least one electrode comprises a stray field electrode;
    the base material comprises an insulating material; and
    the conductive filler comprises at least one metal or carbon black.

3. The apparatus of claim 2, wherein the conductive filler material:
    (a) comprises discrete particles dispersed in a film of the insulating base material;
    (b) comprises at least one metal containing film laminated over at least one base insulating material film; or
    (c) comprises a metal containing film located inside a vessel of the insulating base material.

4. The apparatus of claim 3, wherein:
    the base material comprises at least one of elastomer, rubber, plastic, polymer, ceramic, glass, oxide, nitrate, silicate or carbonate compound, clay, mica and cellulosic material; and
    the conductive filler material comprises at least one of silver, nickel, aluminum, copper, gold, silver plated copper, silver plated aluminum, silver plated nickel, silver plated glass, nickel graphite and alloys thereof.

5. The apparatus of claim 1, wherein the base material comprises a resilient elastomer and the at least one electrode comprises a resilient elastomeric stray field electrode.

6. The apparatus of claim 5, wherein the base material comprises a silicone elastomer film.

7. The apparatus of claim 6, wherein the silicone elastomer film comprises a polyorganosiloxane.

8. The apparatus of claim 7, wherein the polyorganosiloxane comprises polydimethylsiloxane and the conductive filler material comprises silver particles or silver plated copper particles dispersed in the silicone elastomer film.

9. A method for determining a presence of water in a first material, comprising:
    (a) placing a set of electrodes, comprising an insulating base material and a conductive filler material, on a surface of the first material;
    (b) establishing an electric field between the electrodes;
    (c) measuring a phase angle for the electric field at one or more selected frequencies; and
    (d) comparing the measured phase angle value to a predetermined phase angle value corresponding to dry first material, wherein a significant difference between the measured phase angle value and the predetermined phase angle value is indicative of the presence of water in the first material.

10. The method of claim 9, wherein the first material comprises a mica insulation layer in an electrical generator.

11. The method of claim 9, wherein the one or more selected frequencies comprises a frequency selected from about 100 kHz to about 300 kHz.

12. The method of claim 9, wherein:

the electrodes are spaced apart by 0.5 to 2 cm;

the electrodes are rectangular and parallel to each other or interdigitated;

the electric field is established at a voltage of about 100 millivolts to about 2 volts; and the significant difference between the measured phase angle value and the predetermined phase angle value is about 0.3 degrees or more.

13. The method of claim 9, wherein the conductive filler material:

(a) comprises discrete particles dispersed in the insulating base material film;

(b) comprises at least one metal containing film laminated over at least one base insulating material film; or (c) comprises a metal containing film contained inside an insulating base material vessel.

14. The method of claim 13, wherein:

the base material comprises at least one of elastomer, rubber, plastic, polymer, ceramic, glass, oxide, nitrate, silicate or carbonate compound, clay, mica and cellulosic material; and the conductive filler material comprises at least one of carbon black, silver, nickel, aluminum, copper, gold, silver plated copper, silver plated aluminum, silver plated nickel, silver plated glass, nickel graphite and alloys thereof.

15. The method of claim 9, wherein the base material comprises a resilient elastomer and the electrodes comprise resilient elastomeric electrodes.

16. The method of claim 15, wherein the base material comprises a silicone elastomer film.

17. The method of claim 16, wherein the silicone elastomer film comprises a polyorganosiloxane.

18. The method of claim 17, wherein the polyorganosiloxane comprises polydimethylsiloxane and the conductive filler material comprises silver particles or silver plated copper particles dispersed in the silicone elastomer film.

19. An electrical generator, comprising:

(a) an insulating material surrounding at least a portion of an electrically conductive component of the generator;

(b) at least one set of composite stray field electrodes, comprising an insulating base material and a conductive filler material, located on a surface of a first portion of the insulating material;

(c) a power source connected to said at least one set of composite stray field electrodes which permits an establishment of an electrical field between the electrodes;

(d) a phase analyzer for measuring a phase angle associated with the electrical field at one or more selected frequencies; and (e) means for comparing a known phase angle value corresponding to dry insulating material to a measured phase angle value, and for providing an indication of whether water is present in the first portion of the insulating material based on the comparison of the phase angle values.

20. The generator of claim 19, wherein the electrically conductive component comprises a stator bar.

21. The generator of claim 19, wherein the insulating material comprises mica.

22. The generator of claim 19, wherein:

the electrodes are spaced apart by 0.5 to 2 cm;

the electrodes are rectangular and parallel to each other or interdigitated;

the electric field is established at a voltage of about 100 millivolts to about 2 volts;

the one or more selected frequencies are within the range of about 100 kHz to about 300 kHz; and the indication of whether water is present in the first portion of the insulating material comprises a difference between the measured phase angle value and the predetermined phase angle value of about 0.3 degrees or more.

23. The generator of claim 19, wherein the conductive filler material:

(a) comprises discrete particles dispersed in the insulating base material film;

(b) comprises at least one metal containing film laminated over at least one base insulating material film; or (c) comprises a metal containing film contained inside an insulating base material vessel.

24. The generator of claim 23, wherein:

the base material comprises at least one of elastomer, rubber, plastic, polymer, ceramic, glass, oxide, nitrate, silicate or carbonate compound, clay, mica and cellulosic material; and the conductive filler material comprises at least one of carbon black, silver, nickel, aluminum, copper, gold, silver plated copper, silver plated aluminum, silver plated nickel, silver plated glass, nickel graphite and alloys thereof.

25. The generator of claim 19, wherein the base material comprises a resilient elastomer and the electrodes comprise resilient elastomeric electrodes.

26. The generator of claim 25, wherein the base material comprises a silicone elastomer film.

27. The generator of claim 26, wherein the silicone elastomer film comprises a polyorganosiloxane.

28. The generator of claim 27, wherein the polyorganosiloxane comprises polydimethylsiloxane and the conductive filler material comprises silver particles or silver plated copper particles dispersed in the silicone elastomer film.

29. An apparatus for determining a presence of water in a solid insulating material, the apparatus comprising:

a pair of discrete electrodes, each one of the electrodes being disposable on the solid insulating material and comprising a base material; and a conductive filler material comprising a plurality of discrete conductive particles dispersed throughout the base material; and means for measuring a phase angle of an electric field between the electrodes.

30. The apparatus of claim 29, further comprising a processing circuit which compares the measured phase to a predetermined phase signal.

31. The apparatus of claim 30, wherein the predetermined phase signal is indicative of a dry material.

32. A method for determining a presence of water in a solid article, the method comprising the steps of:

placing a set of discrete electrodes on a surface of an article, each of the electrodes comprising an insulating base material and a conductive filler material;

establishing an electric field between the electrodes; and measuring a phase angle of the electric field at one or more frequencies.

33. An electrode comprising:

a pair of discrete electrodes, each one of the electrodes being disposable on a solid insulating material and comprising a base material; and a conductive filler material comprising a plurality of discrete layers of conductive film interlayered with the base material; and a phase analyzer which receives a signal from the electrodes, wherein the phase analyzer measures a phase angle of an electric field between the electrodes.

34. An apparatus for determining a presence of water in a solid article, the apparatus comprising:

a pair of discrete electrodes, each one of the electrodes being disposable on a solid insulating material and comprising a base material; and a conductive filler material comprising a plurality of discrete layers of conductive film interlayered with the base material; and means for measuring a phase angle of an electric field between the electrodes.

* * * * *